(12) United States Patent
Hähnle et al.

(10) Patent No.: US 6,750,262 B1
(45) Date of Patent: Jun. 15, 2004

(54) WATER-ABSORBING, CELLULAR, CROSS-LINKED POLYMERS WITH IMPROVED DISTRIBUTION EFFECT, METHOD FOR THEIR PRODUCTION AND THEIR USE

(75) Inventors: Hans-Joachim Hähnle, Neustadt (DE); Ulrich Schröder, Frankenthal (DE); Wolfgang Heider, Neustadt (DE); Gunnar Schornick, Neuleiningen (DE); Thomas Anstock, Weisenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/926,110

(22) PCT Filed: Feb. 21, 2000

(86) PCT No.: PCT/EP00/01407

§ 371 (c)(1),
(2), (4) Date: Sep. 4, 2001

(87) PCT Pub. No.: WO00/52087

PCT Pub. Date: Sep. 8, 2000

(30) Foreign Application Priority Data

Mar. 3, 1999 (DE) .......................... 199 09 214

(51) Int. Cl.[7] ................. C08J 9/28; C08J 9/30
(52) U.S. Cl. .......................... 521/64; 521/65
(58) Field of Search ..................... 521/65, 64

(56) References Cited

U.S. PATENT DOCUMENTS

| | | | |
|---|---|---|---|
| 4,394,930 A | 7/1983 | Korpman | |
| 4,410,571 A | 10/1983 | Korpman | |
| 4,415,388 A | 11/1983 | Korpman | |
| 4,529,739 A | 7/1985 | Scott et al. | |
| 4,649,164 A | 3/1987 | Scott et al. | |
| 4,725,628 A | 2/1988 | Garvey et al. | |
| 4,725,629 A | 2/1988 | Garvey et al. | |
| 4,731,391 A | 3/1988 | Garvey | |
| 4,808,637 A | 2/1989 | Boardman et al. | |
| 4,985,467 A | 1/1991 | Kelly et al. | |
| 4,990,541 A | 2/1991 | Nielsen et al. | |
| 5,118,719 A | 6/1992 | Lind | |
| 5,182,312 A | 1/1993 | Engelhardt et al. | |
| 5,506,277 A | 4/1996 | Griesbach, III | |
| 5,712,316 A | 1/1998 | Dahmen et al. | |
| 5,750,585 A | 5/1998 | Park et al. | |
| 5,763,067 A | 6/1998 | Brueggemann et al. | |
| 5,844,013 A | 12/1998 | Kenndoff et al. | |
| 5,919,668 A | 7/1999 | Mandai et al. | |
| 6,136,873 A | * 10/2000 | Hahnle et al. | |

FOREIGN PATENT DOCUMENTS

| | | |
|---|---|---|
| DE | 38 31 261 | 3/1990 |
| DE | 196 07 551 | 9/1997 |
| EP | 0 421 264 | 4/1991 |
| EP | 0 427 219 | 5/1991 |
| EP | 0 538 983 | 4/1993 |
| EP | 0 644 207 | 3/1995 |
| WO | WO 88/09801 | 12/1988 |
| WO | WO 94/07935 | 4/1994 |
| WO | WO 94/22502 | 10/1994 |
| WO | WO 95/02002 | 1/1995 |
| WO | WO 95/32860 | 12/1995 |
| WO | WO 96/16099 | 5/1996 |
| WO | WO 96/31555 | 10/1996 |
| WO | WO 97/17397 | 5/1997 |
| WO | WO 98/14508 | 4/1998 |
| WO | WO 99/44648 | 9/1999 |

OTHER PUBLICATIONS

Patent Abstracts of Japan, JP 08–073507, Mar. 19, 1996.
Derwent Publications, AN 1993–402042, KR 9 303 797, May 13, 1993.
Mary T. Clarke, pp. 55–311, "Rheological Additives".

\* cited by examiner

*Primary Examiner*—Morton Foelak
(74) *Attorney, Agent, or Firm*—Oblon, Spivak, McClelland, Maier & Neustadt, P.C.

(57) ABSTRACT

Water-absorbing, expanded, crosslinked polymers obtainable by (I) foaming a polymerizable aqueous mixture which comprises
   (a) monoethylenically unsaturated monomers which contain acidic groups and are optionally neutralized,
   (b) optionally other monoethylenically unsaturated monomers,
   (c) crosslinkers,
   (d) initiators,
   (e) 0.1–20% by weight of at least one surfactant,
   (f) optionally at least one solubilizer and
   (g) optionally thickeners, foam stabilizers, polymerization regulators, fillers and/or cell nucleating agents,
   where the foaming takes place by dissolving a gas which is inert to free radicals under a pressure of 2–400 bar in the polymerizable aqueous mixture, and then decompressing the latter to atmospheric pressure, and (II) polymerizing the foamed mixture to form an expanded hydrogel and, where appropriate, adjusting the water content of the expanded polymer to 1–60% by weight, process for preparing the water-absorbing, expanded, crosslinked polymers and use of these polymers in sanitary articles employed for absorbing body fluids, in dressing material for covering wounds, as sealing material, as soil improver, as soil substitute and as packaging material.

18 Claims, No Drawings

WATER-ABSORBING, CELLULAR, CROSS-LINKED POLYMERS WITH IMPROVED DISTRIBUTION EFFECT, METHOD FOR THEIR PRODUCTION AND THEIR USE

The invention relates to water-absorbing, expanded, crosslinked polymers having an improved distributing action, to a process for the production thereof and to the use thereof in hygiene articles employed to absorb body fluids and in dressing material for covering wounds.

Water-absorbing, crosslinked polymers are referred to as super absorbents or superabsorbing polymers because they are able to absorb a multiple of their own weight of aqueous liquids to form hydrogels. Superabsorbents are used in practice, for example, in diapers for absorbing urine. The superabsorbents have the property of retaining the absorbed liquid even under mechanical stress. They can be in the form of, for example, granules or powders or in expanded form. Two different types of foams are known: (1) mixtures which contain superabsorbents in a foamed matrix, and (2) foams which consist of a superabsorbing material.

A foam belonging to category (1) is produced, for example, from a mixture which comprises, on the one hand, components for forming a polyurethane foam and, on the other hand, polymerizable monomers, a crosslinker and a polymerization initiator to produce a superabsorbent. The foam is formed from the polyurethane components in a mixture of this type in a polycondensation reaction and contains the superabsorbent which has been produced by polymerization of the monomers in the form of an interpenetrating network, cf. U.S. Pat. No. 4,725,628, U.S. Pat. No. 4,725,629 and U.S. Pat. No. 4,731,391.

U.S. Pat. No. 4,985,467 discloses a polyurethane foam which contains a chemically bonded superabsorbent, while WO94/07935, WO95/32860, WO96/16099, WO96/31555 and WO98/14508 describe polyurethane foams containing particles of superabsorbent polymers (SAP) without chemical attachment. Also known are combinations of latex foams into which superabsorbing, fine-particle materials are incorporated after the foaming process, cf. EP-A-427 219 and U.S. Pat. No. 4,990,541. U.S Pat. No. 5,506,277 describes a closed-cell starch foam containing 20–40% superabsorbent.

Foams of this type have the fundamental disadvantage that the superabsorbent present in the foam matrix fills up the pore volume during absorption of aqueous liquids and thus increasingly blocks the pore structure of the foam. These materials therefore show a distinct fall in the absorption speed and an increasing deterioration in the distributing action as absorption increases. This behavior is very disadvantageous for use in hygiene articles.

Products belonging to category (2) of foams are those, for example, which are obtained by mixing a prefabricated superabsorbent in an extruder with a polyhydroxy compound and a blowing agent at elevated temperature. The foam is formed when the mixture is expelled from the extruder. Processes of this type are described, for example, in U.S. Pat. No. 4,394,930, U.S. Pat. No. 4,415,388 and U.S. Pat. No. 4,410,571.

U.S. Pat. No. 4,529,739 and U.S. Pat. No. 4,649,164 disclose processes for producing foams in which a water-swellable polymer having COOH groups is foamed with a blowing agent which liberates the blowing gas in a neutralization reaction with the COOH groups of the polymer.

WO-A-88/09801 discloses that hydrophilic polymers, for example sodium polyacrylate, can be processed in the presence of crosslinkers such as polyepoxides and blowing agents by heating to give an expanded superabsorbent.

According to the statements in WO-A 94/22502, superabsorbing foams based on crosslinked, partially neutralized polycarboxylates are produced by foaming a monomer mixture with a blowing agent which is insoluble in water and has a boiling point below 50° C., and completing polymerization of the foam at virtually the same time as the foaming. The disadvantage of this process is, one the one hand, the use of large amounts of blowing agent, in particular the use of CFC, and, on the other hand, the elaborate monitoring of the process.

EP-A-0421264 discloses the production of foam-like superabsorbents by polymerizing an aqueous monomer mixture which contains an emulsified oil phase. The action of the oil in this case is to occupy the space for the later pores in the foam and it is removed by evaporation, after the polymerization is complete, on drying the expanded material.

Another procedure known for producing expanded superabsorbents is to add carbonates, bicarbonates or carbon dioxide as blowing agents to a mixture of carboxyl-containing monomers, crosslinker and polymerization initiator, with the polymerization of the monomers being started at the same time as the addition of the blowing agent or shortly thereafter. The superabsorbent acquires a foam structure due to the carbon dioxide formed in the neutralization reaction, cf. DE-A 3831261, U.S. Pat. No. 5,118,719, EP-A-538983, U.S. Pat. No. 4,808,637 and U.S. Pat. No. 5,750,585. In the processes disclosed in WO-A 95/02002 and EP-A 644207, an expanded and ground superabsorbent is mixed after production with one or more reactive compounds for subsequent surface crosslinking, and is heated to from 100 to 300° C.

The procedure where the foaming process and the polymerization take place substantially synchronously involves a number of disadvantages. Thus, the resulting foams often have inhomogeneous foam structures containing in some cases considerable amounts of closed-cell structures. In addition, there is a great tendency to skinning, and the resulting materials are hard and brittle. The consequence of these problems is that these foams are used not as whole foams but only in ground form as is stated in the above-mentioned publications. The grinding process eliminates the inhomogeneity described. In addition, this breaks up the closed-cell structures and the skin layers on the foamed material.

JP-A-08073507 describes soft and flexible superabsorbent films which are produced by polymerizing an aqueous acrylate solution, which is partly neutralized by an alkanolamine, in the presence of a crosslinker. Although the resulting films are described as soft and flexible, their use properties are entirely inadequate. Thus, their water absorption speed is much too low for use in hygiene articles, and they moreover show no distributing action and have a pronounced tackiness which greatly restricts handling.

DE-A-19607551 discloses water-absorbing, expanded, crosslinked polymers obtainable by
 (I) foaming a polymerizable aqueous mixture which comprises
  (a) monoethylenically unsaturated monomers which contain acidic groups at least 50% mol are neutralized,
  (b) optionally other monoethylenically unsaturated monomers,
  (c) crosslinkers,
  (d) initiators,
  (e) 0.1–20% by weight of at least one surfactant,
  (f) optionally at least one solubilizer and (g) optionally thickeners, foam stabilizers, polymerization regulators, fillers and/or cell nucleating agents, where the foaming takes place by dispersing fine bubbles of a gas which is inert to free radicals, and (II) polymerizing the foamed mixture to form an expanded hydrogel and, where appropriate, adjusting the water content of the polymer to 1–60% by weight.

A considerable problem in the production of superabsorbing foams from monomer mixtures is the control of the temperature. As explained in detail in WO-A-94/22502 and U.S. Pat. No. 5,750,585, control of the temperature during the foaming and polymerization processes is of crucial importance. Obtaining the required open-cell foam structures is ensured only when the change in temperature is strictly controlled. Control of the temperature during the mechanical blowing in the process of DE-A-19607551 is also of considerable importance because it crucially influences the structure of the monomer foam produced, and thus of the polymer foam.

A strict control of the temperature is always a problem and complicated to implement on the industrial scale when products like foams, which are good insulators, are involved and when large amounts of heat are released at the same time in the process. Large amounts of heat are produced on the one hand by the enormous heat of polymerization of the monomers employed, and on the other hand by the high energy input which occured in the foam production by mechanical blowing in the process of DE-A-19607551.

A fundamental problem for use of superabsorbents in the hygiene industry is their deficient ability to distribute liquids. This deficiency is observed in particular with powdered superabsorbents, but the foams listed above also do not reach the required property level. Increased attention has been directed at this problem recently because of the trend to increasingly thin hygiene articles, for which reason the content of cellulose fluff, which has previously undertaken the distribution, is increasingly being lowered. There is thus a desire for superabsorbing materials which have not only a good storage action and rapid absorption characteristics but, in particular, a pronounced distributing action.

It is an object of the present invention to provide a superabsorbing foam which has a distinctly improved distributing action by comparison with comparable known foams.

We have found that this object is achieved by water-absorbing, expanded, crosslinked polymers obtainable by (I) foaming a polymerizable aqueous mixture which comprises
  (a) monoethylenically unsaturated monomers which contain acidic groups and are optionally neutralized,
  (b) optionally other monoethylenically unsaturated monomers,
  (c) crosslinkers,
  (d) initiators,
  (e) 0.1–20% by weight of at least one surfactant,
  (f) optionally at least one solubilizer and
  (g) optionally thickeners, foam stabilizers, polymerization regulators, fillers and/or cell nucleating agents, where the foaming takes place by dissolving a gas which is inert to free radicals under a pressure of 2–400 bar in the polymerizable aqueous mixture, and then decompressing the latter to atmospheric pressure, and (II) polymerizing the foamed mixture to form an expanded hydrogel and, where appropriate, adjusting the water content of the expanded polymer to 1–60% by weight.

Preferred water-absorbing, expanded, crosslinked polymers are those obtainable by neutralizing the monomers (a) which contain acidic groups using tertiary alkanolamines and/or by neutralizing the free acidic groups of the expanded hydrogel after the polymerization using at least one alkanolamine, the degree of neutralization being at least 20 mol %, and preferably at least 40 mol %, in each case.

The invention additionally relates to a process for producing water-absorbing, expanded, crosslinked polymers, which entails, with a polymerizable mixture of
  (a) monoethylenically unsaturated monomers which contain acidic groups and are optionally neutralized,
  (b) optionally other monoethylenically unsaturated monomers,
  (c) crosslinkers,
  (d) initiators,
  (e) 0.1–20% by weight of at least one surfactant,
  (f) optionally at least one solubilizer and
  (g) optionally thickeners, foam stabilizers, polymerization regulators, fillers and/or cell nucleating agents,
    in a first stage dissolving a gas which is inert to free radicals under a pressure of 2–400 bar in the polymerizable aqueous mixture, then decompressing the latter to atmospheric pressure to form a foam, and in a second stage polymerizing the foam obtained in this way to form an expanded hydrogel and, where appropriate, adjusting the water content of the expanded hydrogel to 1–60% by weight.

This procedure allows reproducible production of superabsorbing foams which, by comparison with conventional SAP foams, have not only an improved distributing action but also faster absorption characteristics and reproducibly homogeneous, open-cell structures without a tendency to skinning. In addition, the problem of controlling the temperature during the production is substantially eliminated. The production of monomer foam takes place virtually without evolution of heat so that control of the temperature is ensured simply by the temperature initially set. The highly exothermic polymerization can be managed adiabatically without this necessarily entailing considerable impairments of the product properties. Another advantage of this process is that the reaction mixtures may have very high solids contents (up to 90%), which makes it possible considerably to reduce the cost of drying.

Any tackiness of the foamed materials can be solved by additional dusting with fine-particle hydrophilic powders.

A polymerizable aqueous mixture is processed according to the invention to a foam which is stable to processing and can be molded as required. The polymerizable aqueous mixture comprises as components (a) monoethylenically unsaturated monomers which contain acidic groups and which are optionally neutralized. Examples of monomers of this type are monoethylenically unsaturated $C_3$–$C_{25}$-carboxylic acids or anhydrides, for example acrylic acid, methacrylic acid, ethacrylic acid, α-chloroacrylic acid, crotonic acid, maleic acid, maleic anhydride, itaconic acid, citraconic acid, mesaconic acid, glutaconic acid, aconitic acid and fumaric acid.

Also suitable as group (a) monomers are monoethylenically unsaturated sulfonic acids, for example vinylsulfonic acid, allylsulfonic acid, sulfoethyl acrylate, sulfoethyl methacrylate, sulfopropyl acrylate, sulfopropyl methacrylate, 2-hydroxy-3-acryl-oxypropylsulfonic acid, 2-hydroxy-3-methacryloxypropylsulfonic acid, vinylphosphonic acid, allylphosphonic acid and 2-acryl-amido-2-methylpropanesulfonic acid. The monomers can be used alone or mixed with one another to produce the superabsorbents. Group (a) monomers which are preferably used are acrylic acid, methacrylic acid, vinylsulfonic acid, acrylamidopropanesulfonic acid or mixtures of these acids, eg. mixtures of acrylic acid and methacrylic acid, mixtures of acrylic acid and acrylamidopropanesulfonic acid or mixtures of acrylic acid and vinylsulfonic acid.

The monomers are optionally neutralized. Alkali metal bases or ammonia or amines are used, for example, for the neutralization. Sodium hydroxide solution or potassium hydroxide solution is preferably used for the neutralization. However, the neutralization can also be carried out with sodium carbonate, sodium bicarbonate, potassium carbonate or potassium bicarbonate or other carbonates or bicarbonates or ammonia. The acidic groups in the monomers are, for example, 15–90 mol % neutralized with at least one of the aforementioned bases.

In one embodiment of the process according to the invention, the monomers (a) are at least 20 mol % neutralized with tertiary alkanolamines. A particularly preferred embodiment is one where at least 40 mol % of the monomers (a) which contain acidic groups are neutralized with tertiary alkanolamines. In this case, the monomers (a) can where appropriate be additionally up to, for example, 100% neutralized with the bases described above, in particular NaOH or ammonia. The degree of neutralization of the monomers (a) which contain acidic groups using tertiary alkanolamines in this variant of the process is 20–95, preferably 30–70, mol %. Tertiary amines which are preferably used are triethanolamine, methyldiethanolamine, dimethylaminodiglycol, dimethylethanolamine and N,N,N',N'-tetra(hydroxyethyl)ethylenediamine.

The polymerizable aqueous mixture may, where appropriate, contain group (b) monomers. By these are meant other monoethylenically unsaturated monomers which are copolymerizable with monomers (a) and (c). These include, for example, the amides and nitriles of monoethylenically unsaturated carboxylic acids, eg. acrylamide, methacrylamide and N-vinylformamide, acrylonitrile and methacrylonitrile, dialkyldiallylammonium halides such as dimethyldiallylammonium chloride, diethyldiallylammonium chloride, allylpiperidinium bromide, N-vinylimidazoles such as N-vinylimidazole, 1-vinyl-2-methylimidazole and N-vinylimidazolines such as N-vinylimidazoline, 1-vinyl-2-methylimidazoline, 1-vinyl-2-ethylimidazoline or 1-vinyl-2-propylimidazoline, which can be used in the form of the free bases, in quaternized form or as salt in the polymerization. Also suitable are dialkylaminoalkyl acrylates and dialkylaminoalkyl methacrylates, dimethylaminoethyl acrylate, dimethylaminoethyl methacrylate, diethylaminoethyl acrylate and diethylaminoethyl methacrylate. The basic esters are preferably used in quaternized form or as salt. Other suitable compounds of group (b) are, for example, vinyl esters of saturated $C_1$–$C_4$-carboxylic acids such as vinyl formate, vinyl acetate or vinyl propionate, alkyl vinyl ethers with at least 2 carbon atoms in the alkyl group, such as ethyl vinyl ether or butyl vinyl ether, esters of monoethylenically unsaturated $C_3$–$C_6$-carboxylic acids, eg. esters of monohydric $C_1$–$C_{18}$-alcohols and acrylic acid, methacrylic acid or maleic acid, monoesters of maleic acid, eg. monomethyl maleate. Other suitable group (b) monomers are styrene, alkyl-substituted styrenes such as ethylstyrene or tert-butylstyrene.

The group (b) monomers can also be used in a mixture with the monomers (a) and (c), eg. mixtures of vinyl acetate and ethyl acrylate in any desired ratio, in the copolymerization.

The group (c) monomers have at least 2 ethylenic double bonds. Examples of monomers of this type, which are normally used as crosslinkers in polymerization reactions, are N,N'-methylenebis-acrylamide, polyethylene glycol diacrylates and polyethylene glycol dimethacrylates which are derived in each case from polyethylene glycols with a molecular weight of from 106 to 8500, preferably 400 to 2000, trimethylolpropane triacrylate, trimethylolpropane trimethacrylate, ethylene glycol diacrylate, propylene glycol diacrylate, butanediol diacrylate, hexanediol diacrylate, hexanediol dimethacrylate, allyl methacrylate, diacrylates and dimethacrylates of block copolymers of ethylene oxide and propylene oxide, polyhydric alcohols such as glycerol or pentaerythritol which are esterified two or three times with acrylic acid or methacrylic acid, triallylamine, tetraallylethylenediamine, divinylbenzene, diallyl phthalate, polyethylene glycol divinyl ethers of polyethylene glycols with a molecular weight of from 106 to 4000, trimethylolpropane diallyl ether, butanediol divinyl ether, pentaerythritol triallyl ether and/or divinylethyleneurea. Water-soluble crosslinkers are preferably used, eg. N,N'-methylenebisacrylamide, polyethylene glycol diacrylates and polyethylene glycol dimethacrylates derived from adducts of 2 to 400 mol of ethylene oxide and 1 mol of a diol or polyol, vinyl ethers of adducts of 2 to 400 mol of ethylene oxide and 1 mol of a diol or polyol, ethylene glycol diacrylate, ethylene glycol dimethacrylate or triacrylates and trimethacrylates of adducts of 6 to 20 mol of ethylene oxide and one mol of glycerol, pentaerythritol triallyl ether and/or divinylurea.

Also suitable as crosslinkers are compounds which contain at least one polymerizable ethylenically unsaturated group and at least one other functional group. The functional group in these crosslinkers must be able to react with the functional groups, essentially the carboxyl groups or sulfo groups, in the monomers (a). Examples of suitable functional groups are hydroxyl, amino, epoxy and aziridino groups.

Also suitable as crosslinkers are those compounds which have at least two functional groups able to react with carboxyl and sulfo groups in the group (a) monomers used. The suitable functional groups have already been mentioned above, ie. hydroxyl, amino, epoxy, isocyanate, ester, amide and aziridino groups. Examples of such crosslinkers are ethylene glycol, diethylene glycol, triethylene glycol, tetraethylene glycol, polyethylene glycol, glycerol, polyglycerol, propylene glycol, polypropylene glycol, block copolymers of ethylene oxide and propylene oxide, sorbitan fatty acid esters, ethoxylated sorbitan fatty acid esters, trimethylolpropane, pentaerythritol, 1,3-butanediol, 1,4-butanediol, polyvinyl alcohol, sorbitol, polyglycidyl ethers such as ethylene glycol diglycidyl ether, polyethylene glycol diglycidyl ether, glycerol diglycidyl ether, glycerol polyglycidyl ether, diglycerol polyglycidyl ether, polyglycerol polyglycidyl ether, sorbitol polyglycidyl ether, pentaerythritol polyglycidyl ether, propylene glycol diglycidyl ether and polypropylene glycol diglycidyl ether, polyaziridine compounds such as 2,2-bishydroxymethylbutanol tris[3-(1-aziridinyl)propionate], 1,6-hexamethylenediethyleneurea, 4,4'-methylenebis(phenyl)-N,N'-diethyleneurea, halo epoxy compounds such as epichlorohydrin and α-methylfluorohydrin, polyisocyanates such as 2,4-tolylene diisocyanate and hexamethylene diisocyanate, alkylene carbonates such as 1,3-dioxolan-2-one and 4-methyl-1,3-dioxolan-2-one, polyquaternary amines such as condensates of dimethylamine with epichlorohydrin, homo- and copolymers of diallyldimethylammonium chloride, and homo- and copolymers of dimethylaminoethyl (meth)acrylate, which are, where appropriate, quaternized with, for example, methyl chloride.

Other suitable crosslinkers are polyvalent metal ions able to form ionic crosslinks. Examples of such crosslinkers are magnesium, calcium, barium and aluminum ions. These crosslinkers are added, for example, as hydroxides, carbonates or bicarbonates to the aqueous polymerizable solution. A particularly preferred crosslinker of this type is sodium aluminate.

Other suitable crosslinkers are multifunctional bases which are likewise able to form ionic crosslinks, for example polyamines or their quaternized salts. Examples of polyamines are ethylenediamine, diethylenetriamine, triethylenetetramine, tetraethylenepentamine, pentaethylenehexamine and polyethyleneimines, and polyvinylamines with molecular weights of up to 4,000,000 in each case.

In a preferred embodiment of the invention, two different crosslinkers are used, one of which is soluble in water and the other is insoluble in water. The hydrophilic crosslinker which is soluble in the aqueous phase of the reaction mixture produces, in a conventional way, a relatively uniform crosslinking of the resulting polymer, as is conventional in the production of a superabsorbent. The hydrophobic crosslinker which is insoluble or has only limited solubility in the polymerizable aqueous mixture concentrates in the surfactant interlayer between the gas phase and the polymerizable aqueous phase. This means that, in the subsequent polymerization, the surface of the foam is more extensively crosslinked than is the interior of the superabsorbent hydrogel. This results in a core/shell structure of the foam directly in the production of the superabsorbent foam. Such extensive surface crosslinking of a superabsorbent foam is possible in the prior art production processes only by subsequent surface crosslinking of an expanded superabsorbent which has already been formed. In the conventional procedure, a separate process step is necessary for this subsequent crosslinking, but this can be omitted in the process of the present invention.

Products according to the invention with a core/shell structure show distinctly improved properties compared with homogeneously crosslinked samples in respect of the absorption speed, distributing effect and gel stability. Apart from polyvalent metal ions, all the water-insoluble crosslinkers which are described above and can be assigned to the various groups are suitable for producing foams with a core/shell structure, ie. foams in which the entire surface is more highly crosslinked than the layer underneath, which has been referred to above as the core layer. Particularly preferred hydrophobic crosslinkers are diacrylates or dimethacrylates or divinyl ethers of alkanediols with 2 to 25 carbon atoms (branched, linear, with any suitable arrangement of OH groups) such as 1,3-propanediol, 1,4-butanediol, 1,6-hexanediol, neopentyl glycol, 1,9-nonanediol or 1,2-dodecanediol, di-, tri- or polypropylene glycol diacrylates or dimethacrylates, allyl acrylate, allyl methacrylate, divinylbenzene, glycidyl acrylate or glycidyl methacrylate, allyl glycidyl ether and bisglycidyl ethers of the alkanediols listed above.

Examples of suitable hydrophilic crosslinkers are N,N'-methylenebisacrylamide, polyethylene glycol diacrylates or dimethacrylates with a molecular weight $M_N$ of from 200 to 4000, divinylurea, triallylamine, diacrylates or dimethacrylates of adducts of from 2 to 400 mol of ethylene oxide and 1 mol of a diol or polyol or the triacrylate of an adduct of 20 mol of ethylene oxide and 1 mol of glycerol and vinyl ethers of adducts of from 2 to 400 mol of ethylene oxide and 1 mol of a diol or polyol.

The group (a) monomers are present in the polymerizable aqueous mixture in amounts of, for example, from 10 to 90, and preferably 20 to 85, % by weight. The group (b) monomers are used only where appropriate for modifying the superabsorbent foams and can be present in amounts of up to 50, preferably in amounts of up to 20, % by weight in the polymerizable aqueous mixture. The crosslinkers (c) are present in the reaction mixture in amounts of, for example, from 0.001 to 12, and preferably from 0.01 to 8, % by weight.

The polymerization initiators which can be used are all initiators which form free radicals under the polymerization conditions and which are normally used in the preparation of superabsorbents. It is also possible to initiate the polymerization by the action of electron beams on the polymerizable aqueous mixture. However, the polymerization can also be started in the absence of initiators of the abovementioned type by the action of high-energy radiation in the presence of photoinitiators.

Polymerization initiators which can be used are all compounds which decompose to free radicals under the polymerization conditions, eg. peroxides, hydroperoxides, hydrogen peroxide, persulfates, azo compounds and the redox catalysts. Water-soluble initiators are preferably used. It is advantageous in some cases to use mixtures of various polymerization initiators, eg. mixtures of hydrogen peroxide and sodium or potassium peroxydisulfate. Mixtures of hydrogen peroxide and sodium peroxydisulfate can be used in any desired ratio. Examples of suitable organic peroxides are acetylacetone peroxide, methyl ethyl ketone peroxide, tert-butyl hydroperoxide, cumene hydroperoxide, tert-amyl perpivalate, tert-butyl perpivalate, tert-butyl perneohexanoate, tert-butyl perisobutyrate, tert-butyl per-2-ethylhexanoate, tert-butyl perisononanoate, tert-butyl permaleate, tert-butyl perbenzoate, di(2-ethylhexyl) peroxydicarbonate, dicyclohexyl peroxydicarbonate, di(4-tert-butylcyclohexyl) peroxydicarbonate, dimyristyl peroxydicarbonate, diacetyl peroxydicarbonate, allyl peresters, cumyl peroxyneodecanoate, tert-butyl per-3,5,5-trimethylhexanoate, acetyl cyclohexylsulfonyl peroxide, dilauroyl peroxide, dibenzoyl peroxide and tert-amyl perneodecanoate. Particularly suitable polymerization initiators are water-soluble azo initiators, eg. 2,2'-azobis(2-amidinopropane) dihydrochloride, 2,2'-azobis(N,N'-dimethyleneisobutyramidine) dihydrochloride, 2-(carbamoylazo)isobutyronitrile, 20 2,2'-azobis[2-(2-imidazolin-2-yl)propane] dihydrochloride and 4,4'-azobis(4-cyanovaleric acid). Said polymerization initiators are used in conventional amounts, eg. in amounts of from 0.01 to 5, preferably 0.1 to 2.0, % of the weight of the monomers to be polymerized.

Also suitable as initiators are redox catalysts. The redox catalysts contain as oxidizing component at least one of the abovementioned peroxy compounds and as reducing component, for example, ascorbic acid, glucose, sorbose, ammonium or alkali metal bisulfite, sulfite, thiosulfate, hyposulfite, pyrosulfite or sulfide, metal salts such as iron(II) ions or silver ions, or sodium hydroxymethylsulfoxylate. The reducing component preferably used in the redox catalyst is ascorbic acid or sodium sulfite. Based on the amount of monomers used in the polymerization, for example, from $3 \times 10^{-6}$ to 1 mol % of the reducing component of the redox catalyst system and from 0.001 to 5.0 mol % of the oxidizing component of the redox catalyst are used.

If the polymerization is initiated by the action of high-energy radiation, photoinitiators are normally used as initiator. These may be, for example, α-splitters, H-abstracting systems or else azides. Examples of initiators of these types are benzophenone derivatives such as Michler's ketone, phenanthrene derivatives, fluorene derivatives, anthraquinone derivatives, thioxanthone derivatives, coumarin derivatives, benzoin ethers and derivatives thereof, azo compounds like the free-radical formers mentioned above, substituted hexaarylbisimidazoles or acylphosphine oxides.

Examples of azides are: 2-(N,N-dimethylamino)ethyl 4-azidocinnamate, 2-(N,N-dimethylamino)ethyl 4-azidonaphthyl ketone, 2-(N,N-dimethylamino)ethyl 4-azidobenzoate, 5-azido-1-naphthyl 2-(N,N-dimethylamino)ethyl sulfone, N-(4-azidosulfonylphenyl) maleimide, N-acetyl-4-azidosulfonylaniline, 4-azidosulfonylaniline, 4-azidoaniline, 4-azidophenacyl bromide, p-azidobenzoic acid, 2,6-bis(p-azidobenzylidene) cyclohexanone and 2,6-bis(p-azidobenzylidene)-4-methylcyclohexanone. The photoinitiators are, if employed, normally used in amounts of from 0.01 to 5% of the weight of the monomers to be polymerized.

The polymerizable aqueous mixtures contain as component (e) from 0.1 to 20% by weight of at least one surfactant. The surfactants are of crucial importance for the production and stabilization of the foam. Anionic, cationic or nonionic surfactants or mixtures of surfactants which are compatible with one another can be used. It is possible to employ low molecular weight or else polymeric surfactants, and combinations of different or else similar types of surfactants have proved to be advantageous. Examples of nonionic surfactants are adducts of alkylene oxides, in particular ethylene oxide, propylene oxide and/or butylene oxide, and alcohols, amines, phenols, naphthols or carboxylic acids. Surfactants advantageously used are adducts of ethylene oxide and/or propylene oxide and alcohols containing at least 10 carbon atoms, where the adducts contain from 3 to 200 mol of ethylene oxide and/or propylene oxide per mol of alcohol. The adducts contain the alkylene oxide units in the form of blocks or in random distribution. Examples of nonionic surfactants are the adducts of 7 mol of ethylene oxide and 1 mol of tallow fatty alcohol, products of the reaction of 9 mol of ethylene oxide with 1 mol of tallow fatty alcohol and adducts of 80 mol of ethylene oxide and 1 mol of tallow fatty alcohol. Other commercial nonionic surfactants consist of products of the reaction of oxo alcohols or Ziegler alcohols with 5 to 12 mol of ethylene oxide per mol of alcohol, in particular with 7 mol of ethylene oxide. Other commercial nonionic surfactants are obtained by ethoxylation of castor oil. For example, from 12 to 80 mol of ethylene oxide are added on per mol of castor oil. Further commercial products are, for example, the products of the reaction of 18 mol of ethylene oxide with 1 mol of tallow fatty alcohol, the adducts of 10 mol of ethylene oxide and 1 mol of a $C_{13}/Cl_{15}$ oxo alcohol, or the products of the reaction of 7 to 8 mol of ethylene oxide and 1 mol of a $C_{13}/C_{15}$ oxo alcohol. Other suitable nonionic surfactants are phenol alkoxylates such as p-tert-butylphenol which has been reacted with 9 mol of ethylene oxide, or methyl ethers of products of the reaction of 1 mol of a $C12-C_{18}$-alcohol and 7.5 mol of ethylene oxide.

The nonionic surfactants described above can be converted, for example, by esterification with sulfuric acid into the corresponding sulfuric acid half esters. The sulfuric acid half esters are employed as anionic surfactants in the form of the alkali metal or ammonium salts. Examples of suitable anionic surfactants are alkali metal or ammonium salts of sulfuric acid half esters of adducts of ethylene oxide and/or propylene oxide and fatty alcohols, alkali metal or ammonium salts of alkylbenzenesulfonic acid or of alkylphenol ether sulfates. Products of said type are commercially available. Examples of commercial anionic surfactants are the sodium salt of a sulfuric acid half ester of a $C_{13}/C_{15}$ oxo alcohol which has been reacted with 106 mol of ethylene oxide, the triethanolamine salt of dodecylbenzenesulfonic acid, the sodium salt of alkylphenol ether sulfates and the sodium salt of the sulfuric acid half ester of a product of the reaction of 106 mol of ethylene oxide with 1 mol of tallow fatty alcohol. Other suitable anionic surfactants are sulfuric acid half esters of $C_{13}/C_{15}$ oxo alcohols, paraffinsulfonic acids such as $C_{15}$-alkylsulfonate, alkyl-substituted benzenesulfonic acids and alkyl-substituted naphthalenesulfonic acids such as dodecylbenzenesulfonic acid and di-n-butylnaphthalenesulfonic acid, and fatty alcohol phosphates such as $C_{15}/C_{18}$ fatty alcohol phosphate. The polymerizable aqueous mixture may contain combinations of a nonionic surfactant and an anionic surfactant or combinations of nonionic surfactants or combinations of anionic surfactants. Cationic surfactants are also suitable. Examples thereof are the products, quaternized with dimethyl sulfate, of the reaction of 6.5 mol of ethylene oxide with 1 mol of oleylamine, distearyldimethylammonium chloride, lauryltrimethylammonium chloride, cetylpyridinium bromide and the triethanolamine ester of stearic acid which is quaternized with dimethyl sulfate and is preferably used as cationic surfactant.

The surfactant content of the polymerizable aqueous mixture is preferably 0.5 to 10, % by weight. In most cases, the polymerizable aqueous mixtures have a surfactant content of from 1.5 to 8% by weight.

The polymerizable aqueous mixtures may contain as component (f), where appropriate, at least one solubilizer. By this are meant water-miscible organic solvents, eg. alcohols, glycols, polyethylene glycols and monoethers derived therefrom, the monoethers containing no double bonds in the molecule. Suitable ethers are methylglycol, butylglycol, butyldiglcyol, methyldiglycol, butyltriglycol, 3-ethoxy-1-propanol and glycerol monomethyl ether.

The polymerizable aqueous mixtures contain 0 to 50% by weight of at least one solubilizer. If solubilizers are used, their content in the polymerizable aqueous mixture is preferably 1 to 25% by weight.

The polymerizable aqueous mixture may, where appropriate, contain thickeners, foam stabilizers, polymerization regulators, fillers and cell nucleating agents. Thickeners are used, for example, to optimize the foam structure and to improve the foam stability. This results in only slight shrinkage of the foam during the polymerization. Suitable thickeners are all natural and synthetic polymers which are known for this purpose and which greatly increase the viscosity of an aqueous system. These may be water-swellable or water-soluble synthetic and natural polymers. Superabsorbents in powder form are also suitable as thickeners. A detailed review of thickeners is to be found, for example, in the publications by R. Y. Lochhead and W. R. Fron, Cosmetics & Toiletries, 108, 95–135 (May 1993) and M. T. Clarke, "Rheological Additives" in D. Laba (Ed.) "Rheological Properties of Cosmetics and Toiletries", Cosmetic Science and Technology Series, Vol. 13, Marcel Dekker Inc., New York 1993.

Water-swellable or water-soluble synthetic polymers suitable as thickeners are, for example, high molecular weight polymers of the monoethylenically unsaturated monomers which contain acidic groups described above under (a). Examples of thickeners of this type are high molecular weight homopolymers of acrylic acid and/or methacrylic acid or slightly crosslinked copolymers of acrylic acid and/or methacrylic acid and a compound which contains at least 2 ethylenic double bonds, eg. butanediol diacrylate. Also suitable are high molecular weight polymers of acrylamide and methacrylamide or copolymers of acrylic acid and acrylamide with molecular weights of more than 1 million. Copolymers of this type are known as thickeners. Other known thickeners are high molecular weight polyethylene glycols or copolymers of ethylene glycol and propylene glycol, and high molecular weight polysaccharides such as starch, guar gum, locust bean gum or derivatives of natural substances such as carboxymethylcellulose, hydroxyethylcellulose, hydroxymethylcellulose, hydroxypropylcellulose and cellulose mixed ethers. Another group of thickeners comprises water-insoluble products such as finely divided silicon dioxide, pyrogenic silicas, precipitated silicas in hydrophilic or hydrophobic modifications, zeolites, titanium dioxide, cellulose powder, or other fine-particle powders of crosslinked polymers which are different from superabsorbents. The polymerizable aqueous mixtures may contain the thickeners in amounts of up to 30% by weight. If such thickeners are in fact used, they are present in the polymerizable aqueous mixture in amounts of from 0.1, preferably 0.5, to 20% by weight.

In order to optimize the foam structure, it is possible where appropriate to add hydrocarbons with at least 5 carbon atoms in the molecule to the aqueous reaction mixture. Examples of suitable hydrocarbons are pentane, hexane, cyclohexane, heptane, octane, isooctane, decane and dodecane. The suitable aliphatic hydrocarbons may be straight-chain, branched or cyclic and have a boiling point which is above the temperature of the aqueous mixture during the foaming. The aliphatic hydrocarbons increase the pot life of the foamed aqueous reaction mixture which has not yet polymerized. This facilitates the handling of the foams which have not yet polymerized and increases the reliability of the process. The hydrocarbons are used in amounts of from 0 to 10% of the weight of the polymerizable aqueous mixture. When they are used, the amounts preferably present in the aqueous mixture are from 0.1 to 5% by weight.

In order to alter the properties of the superabsorbents, for example the absorption speed and the absorption capacity for water, it may be advantageous to add a polymerization regulator or a mixture of several polymerization regulators to the aqueous reaction mixture. Examples of suitable polymerization regulators are formic acid, thio compounds such as 2-mercaptoethanol, mercaptopropanol, mercaptobutanol, dodecyl mercaptan, thio-glycolic acid or amides such as ethanolamine, diethanolamine, triethanolamine, or amines such as triethylamine, morpholine or piperidine. The amounts of polymerization regulators can be up to 10% of the weight of the monomers used. If polymerization regulators are used, preferably from 0.1 to 5% of the weight of the monomers is used.

The constituents indicated under (g) which are to be used optionally, can be employed singly or in a mixture in the production of the polymers according to the invention. However, the absence of thickeners, foam stabilizers, fillers, cell nucleating agents and polymerization regulators is also possible.

In the production, according to the invention, of water-absorbing, expanded, crosslinked polymers, the first stage of the process is foaming of the polymerizable aqueous mixture described above. For this purpose, the aqueous monomer phase is charged under a pressure of 2–400 bar, preferably 5–40 bar, with a gas which is inert to free radicals, whereupon, for example, at least 1.0 g of the inert gas dissolved per kg of the polymerizable mixture. A particularly preferred procedure is one in which a polymerizable mixture saturated with inert gases is prepared under the stated pressure conditions. Examples of inert gases suitable for the process according to the invention are carbon dioxide, nitrogen and dinitrogen monoxide. It is also possible to use, for example, mixtures of carbon dioxide and nitrogen in any desired ratio. Carbon dioxide is the gas preferably employed. The use of carbon dioxide as gas which is inert to free radicals, at least 2.0 g of carbon dioxide, preferably 8–30 g, are required, for example, for foaming 1 kg of the aqueous polymerizable monomer mixture. The dissolving of the inert gases in the aqueous polymerizable mixtures, preferably the preparation of saturated aqueous polymerizable mixtures, can take place in batch operation or else continuously. The gas-saturated monomer phase is then decompressed to atmospheric pressure. This forms a fine-particle, closed-cell monomer foam which is stable for a prolonged period. Typical pot lives vary between 10 min and several hours.

The decompression can take place in one or else in several pressure drops. In the simplest case, the reaction mixture flows under pressure out through a nozzle. It may be advantageous to use special techniques to optimize the monomer foam structure. Thus, it is possible to use a mixing nozzle which mixes an additional gas stream into the emerging stream of the reaction mixture, and the gas admixed in this case can be identical to or different from that used for the saturation. The admixing of the gas during the decompression creates nuclei for the release of the dissolved gas, by which means it is possible specifically to influence the structure of the monomer foam. Another possibility for generating nuclei during the decompression is to pass the reaction mixture immediately before the decompression through a unit containing a cavitating impeller. It may further be advantageous to direct the emerging liquid stream against a deflector, in which case the foam is formed on impact with the deflector. This procedure has the advantage that the foam acquires a homogeneous pore size distribution. If, instead of this, the jet of liquid is introduced directly into the foam, additional gas bubbles are introduced into the foam in the wake of the jet of liquid, which usually broadens the size distribution of the bubbles.

An expedient procedure is first to dissolve all the water-soluble components in water and only then to add the water-insoluble substances. Depending on the initiator employed, it may be advantageous to add the initiator only at the end of the saturation process. The consistency of the foams can be varied within a relatively wide range. Thus, it is possible to produce either foams which flow readily or else rigid, as yet unpolymerized foams which can be cut. It is likewise possible to vary the average size of the gas bubbles, their size distribution and their arrangement in the liquid matrix by the selection of the surfactants, the solubilizers, thickeners and foam stabilizers, cell nucleating agents, the temperature, the saturating pressure and the nucleation measures described above within a wide range so that it is possible in a simple way to adjust the density or wall thickness of the matrix material. The temperatures of the polymerizable aqueous mixture during the foaming step are in the range from −20 to 100, preferably −5 to +40° C.

It is possible in a simple manner deliberately to adjust particular foam densities by suitable choice of the gas employed and the saturating pressure. Since the resulting monomer foams are stable and easily handled over lengthy periods, for example up to 6 hours, they can be placed in a suitable mold for the subsequent polymerization in order to produce molded articles required for a particular application. Waste foam which is possibly produced on shaping the foamed polymerizable aqueous mixture can be returned directly to the process. The foamed polymerizable material can, for example, be applied in the required thickness to a temporary substrate, which is advantageously provided with a non-stick coating. It is possible, for example, to apply the foam to a substrate with a knife. Another possibility is to introduce the polymerizable expanded aqueous mixture into molds which likewise have a non-stick coating, and to polymerize the foam completely therein.

Since the foamed polymerizable aqueous mixture has a long pot life, this mixture is also suitable for producing composite materials. Thus, for example, the polymerizable foam produced mechanically can be applied to a permanent substrate, eg. sheets composed of polymers (eg. polyethylene, polypropylene or polyamide sheets) or metals, nonwovens, fluff, tissues, woven fabric, natural or synthetic fibers, or to other foams. In the production of composite materials it may in some circumstances also be advantageous to apply the polymerizable foam in the form of particular structures or in layers differing in thickness to a substrate. However, it is also possible to apply the polymerizable foam to fluff layers and to impregnate them in such a way that the fluff is, after the polymerization, an integral constituent of the foam. The foamed polymerizable aqueous mixture obtainable in the first stage of the process can also be shaped to large blocks and polymerized. The blocks can, after the polymerization, be cut or sawn to smaller shaped articles. It is also possible to produce sandwich-like structures by applying a foamed polymerizable aqueous mixture to a substrate, to cover the expanded layer with a sheet, nonwovens, tissues, woven fabrics, fibers or other foams, where appropriate of a material differing from the one used first, and again to apply foam and, where appropriate, to cover with another sheet, nonwovens, tissues, woven fabrics, fibers or other foams. The composite is then subjected to the polymerization in the second stage of the process. However, sandwich-like structures with other foam layers can also be produced.

In the second stage of the process for producing the superabsorbing foams according to the invention, the foamed polymerizable aqueous mixture is polymerized. The polymerization can take place, depending on the initiator used, by increasing the temperature, by exposure to light, by exposure to electron beams or else by increasing the temperature and exposing to light. The temperature of the foamed polymerizable aqueous mixture can be increased by using all processes customary in industry, for example bringing the foam into contact with heatable plates, exposure of the polymerizable foam to infrared radiation, or heating with microwaves. Foam layers according to the invention with a thickness of up to about 1 millimeter are produced, for example, by heating one side or, in particular, by irradiation on one side. If relatively thick layers of a foam are to be produced, eg. foams with thicknesses of several centimeters, heating of the polymerizable foamed material by microwaves is particularly advantageous because relatively uniform heating can be achieved in this way. The polymerization is carried out, for example, at temperatures from 20 to 180, preferably in the range from 20 to 100, ° C.

Foam layers of intermediate thicknesses, i.e. with a thickness in the range from about 1 millimeter to about 2 centimeters, such as from about 2 millimeters to about 1 centimeter, are preferably produced in the following way: instead of initiating the polymerization on only one surface, initiation is brought about on both surfaces by exposing a layer of the composition foamed according to the invention to heat treatment and/or irradiation with light on both surfaces. Treatment of both surfaces of the foam layer can take place according to the invention synchronously or asynchronously in any time sequence or in a deferred fashion. It is possible, for example, for the heat treatment of both surfaces of a foam layer to be carried out simultaneously or in a deferred fashion on one occasion or several occasions per surface. The procedure on irradiation with light can be likewise. However, it is also possible to treat each surface both with heat and with light, and exposure to heat and light can take place simultaneously or in any sequence, on one occasion or several times on the same surface of the foam layer. However, it is usually most expedient to use heat and/or light once on each surface of the foam layer.

Since the heat treatment expediently takes place by contact heating, and the support material used for this purpose usually does not transmit light, polymerization initiation on both sides is most expediently carried out by contact heating one surface and, for example simultaneously, irradiating the opposite surface. This variant of the process, and the contact heating on both sides, are particularly suitable for producing composite materials.

The heat treatment usually takes place in the case of polymerisation initiation on both surfaces in a range from about 50 to about 200° C., preferably at about 80 to about 160° C. Typical contact times are in this case about 0.5 to about 25 minutes for each surface of the film layer, preferably about 2 to about 15 minutes. The light used for the irradiation is preferably from the UV/VIS region, i.e. light from the ultraviolet or visible region of the spectrum, such as, for example, light with a wavelength in the range from about greater than 200 nm up to about 750 nm, for example about 250 nm to about 700 nm, such as, for example, UV-A radiation of wavelength 315 to 400 nm. The duration of the irradiation can likewise be in the range from about 0.1 to about 25 minutes, preferably about 0.5 to 10 minutes, for each surface of the foam layer.

On combined heat treatment and irradiation of the same or opposite surfaces of the foam layer, the respective duration of heat treatment and irradiation can be identical or different. Depending on the composition and thickness of the foam layer, nature and quantity of the polymerization initiators used, intensity and wavelength of the light, and temperature of the contact heating device and other criteria, however, it may be advantageous to carry out the heat treatment and irradiation over time intervals of different lengths. The chosen time intervals may, for example, follow one another in time. For example, heating of the first surface for, for example, 3 minutes can be followed by irradiation of the opposite second surface for, for example, 2 minutes. This can be followed where appropriate by a heat treatment of the first and/or the second surface for, for example, 2 minutes. This treatment rhythm can, where appropriate, be repeated one more times with retention or alteration of the chosen time intervals. The chosen time intervals may, however, also overlap. For example, in this case the irradiation can be maintained for only part of the heat-treatment interval. Thus, for example, the first surface of the foam layer can be heated, for example, for 2 minutes and then heated, for example, for a further 4 minutes and, synchronously with this, the opposite surface can be irradiated for 4 minutes. It is likewise conceivable initially to heat or to irradiate the two surfaces synchronously for, for example, 3 minutes and then to continue the heat treatment of one surface, for example for 2 minutes, after the irradiation of the other surface has been completed. These treatment rhythms can also be repeated one or more times where appropriate with retention or alteration of the chosen time intervals.

When the polymerization is initiated by exposing the foamed polymerizable material to light it is possible to use all conventional light-exposure systems as long as their emission spectrum is suited to the photoinitiator used. When the polymerization is initiated by exposure to light it is advantageous to use a combination of a photoinitiator and a thermal initiator and/or a photoinitiator which can also act as thermal initiator, eg. azo initiators. Since the foam becomes very hot during the polymerization due to the high heat of polymerization, the polymerization reaction takes place particularly fast and efficiently in this way. On initiation by exposure to light, the polymerization temperature is in the range from 0 to 150, preferably 10 to 100, ° C.

During the polymerization, the density of the foam changes negligibly. However, the initially closed-cell structure opens in such a way that the membranes between adjacent foam bubbles rupture and thus windows (passages) are formed between the individual pores. This process results in the final product of the polymerization as a substantially, but preferably completely, open-celled foam. The polymerization reaction, and this opening mechanism is influenced by the starting temperature, the initiation technique or the removal of heat. The polymerization temperature is preferably controlled in such a way that boiling of the polymerizable aqueous mixture is avoided. As polymerization advances, the foam consolidates as a result of increasing gel formation.

The foams resulting after the polymerization have a water content between 5% and 80%. It is possible in principle by using alkanolamines to obtain foams which are flexible even in the dried state. However, since the foams are hygroscopic and anyway absorb moisture from the air, it is sensible to leave a residual moisture content in the region of 0.1–20, preferably 1–15, % by weight in the foam. It may also be worthwhile, depending on the composition of the foam and the intended area of use, to adjust the moisture content in the foam to differ from this.

The foam can be dried by all conventional techniques, for example by heating with a stream of hot gas, by reducing the pressure, by exposure to infrared radiation or by heating with microwaves. Microwaves once again proved to be advantageous in this case for drying large-volume shaped articles. The temperature during the drying should be less than 180° C., preferably less than 120° C. It may be advantageous to dry with a stream of gas having a defined moisture content (up to the use of steam) so that the foam is dried only to a defined moisture content in this way.

Compared with previously disclosed superabsorbents in foam form, a considerable advantage of the foams according to the invention is to be seen in the fact that they have an improved ability to distribute aqueous liquids over the entire absorption core of a hygiene article. The technique of foam production according to the invention has the advantage that the temperature control, as a critical parameter in the foam production process, is considerably simplified and thus the process reliability and reproducibility are increased.

The process according to the invention results in an open-celled superabsorbent foam which is predominantly, preferably at least 80%, open-celled. The water-absorbing, expanded, crosslinked polymers which can be produced in this way have a free absorption speed (FAS) for a 0.9% by weight aqueous sodium chloride solution of from 4.0 to 100 g/g sec. They have a vertical wicking time (VWT=time for spreading of a 0.9% by weight aqueous sodium chloride solution in the vertical direction in a foam) of from 0.2 to 120 seconds for a height of 4 cm.

As indicated above, an inhomogeneous crosslink density can be produced even during the production of the superabsorbent foams according to the invention. This is particularly advantageous when the monomers used as the components, described above, are (a) acrylic acid, methacrylic acid, vinylsulfonic acid, acrylamidopropanesulfonic acid or mixtures thereof, and (c) a mixture of at least one water-soluble and at least one water-insoluble crosslinker.

It may, nevertheless, be desirable subsequently to alter the degree of crosslinking of the foam. In order to achieve this, for example, it is possible to incorporate latent crosslinkage points in the gel during the polymerization by adding suitable monomers, these points not leading to crosslinking reactions under the conditions of production of the foam but being able under specific conditions which can be applied subsequently, eg. by greatly increasing the temperature, to form further crosslinkage points in the gel structure. Examples which can serve for such monomers are hydroxyl-containing compounds which are able at elevated temperature, ie. above 150° C., to react with the carboxyl groups in the foam structure. Examples of compounds suitable as latent crosslinkage points are hydroxyethyl acrylate, hydroxypropyl acrylate, hydroxybutyl acrylate, monoacrylic esters of glycerol, monoacrylates or monometh-acrylates of polyethylene glycols with at least 2 ethylene glycol units, monoacrylates or monomethacrylates of polypropylene glycols with at least 2 propylene glycol units and monomethacrylates of polyhydric alcohols, eg. hydroxybutyl methacrylate, hydroxypropyl methacrylate, hydroxyethyl methacrylate or glycerol monomethacrylate.

Another possibility for homogeneous subsequent crosslinking is provided by subsequent addition of crosslinking reagents, ie. compounds which have at least two reactive groups which are able, under suitable conditions, eg. on heating above 70° C., to react with the acidic groups in the expanded hydrogel. In this case it is also possible to achieve, controlled by the depth of penetration of the crosslinker, a modification of the inhomogeneous crosslink density. Suitable crosslinkers form covalent or ionic bonds with the carboxyl groups of the polymer matrix. Suitable crosslinkers are compounds which have at least two functional groups of the same or different types, eg. hydroxyl, amino, quaternary ammonium, isocyanato, epoxy, aziridino, ester or amide groups. Preferred subsequent crosslinkers are polyalcohols such as glycerol, butylene glycol or propylene glycol but also bisepoxides or functionalized silanes. Reaction with such crosslinkers can take place for example in the temperature range 10–170, preferably 20–160° C. The application of the crosslinkers to the foamed material can take place, for example, by spraying, dipping or gas-deposition.

It is possible according to the invention to produce a foam with a lower degree of neutralization, typically between 0 and 60%, preferably 15 to 40%, and definitively intended and to apply at least one alkanolamine subsequently for neutralizing the acidic groups of the superabsorbing polymers, for example by spraying on the alkanolamines or solutions thereof in solvents or solvent mixtures. Examples of solvents which can be used for alkanolamines are: water, methanol, ethanol, isopropanol and acetone. Water is preferred. The subsequent neutralization expediently takes place after the polymerization and before the drying.

However, it is also possible to apply at least one alkanolamine to the expanded hydrogel at a later time during the process.

This procedure is obligatory for use in secondary and primary alkanolamines. Tertiary alkanolamines can—as described above—be employed to neutralize the monomers (a) and, in addition—just like primary, secondary and quaternary alkanolamines, be used to neutralize the acidic groups in the expanded hydrogel after the polymerization. In some cases it has emerged that an advantageous procedure is for the monomers (a) containing acidic groups to be firstly partially neutralized with a tertiary alkanolamine (e.g. 20–50 mol %) and then polymerized, and subsequently for the remaining free acidic groups in the expanded hydrogel to be neutralized with an alkanolamine, preferably a primary alkanolamine such as ethanolamine, with the total degree of neutralization of the acidic groups in the hydrogel being 55 to 95, preferably 65 to 85, mol %.

The alkanolamines used can be primary, secondary, tertiary or quaternary and be monofunctional, difunctional or polyfunctional bases. The alkanolamines may in addition to their amino and hydroxyl groups have other functional groups such as ester, urethane, ether, thioether and urea groups. It is possible to employ, for example, low molecular weight compounds such as triethanolamine, methyldiethanolamine, dimethylethanolamine, ethanolamine, N-hydroxyethylmorpholine, dimethylaminodiglycol, N,N,N',N'-tetra(hydroxyethyl) ethylenediamine, N,N,N',N'-tetra(hydroxypropyl) ethylenediamine, dimethylaminotriglycol, diethylaminoethanol, 3-dimethylamino-1,2-propanediol, triisopropanolamine, diisopropylaminoethanol, choline hydroxide, choline carbonate, 2-tert-butylaminoethanol, tris (hydroxymethyl)aminomethane, 3 amino-1-propanol, isopropanolamine, 2-(2-aminoethoxy)ethanol, 2-amino-2-methyl-1-propanol or else oligomers or polymers such as polymers or condensates with amino groups, such as polyethyleneimines or polyvinylamines, which have been reacted with ethylene oxide, propylene oxide, glycidol or other epoxides, or products of the reaction of at least bifunctional, low molecular weight alkanolamines with at least bifunctional reagents able to react either with the hydroxyl or with the amino group of the alkanolamines, such as carboxylic acids, esters, epoxides, isocyanates.

Suitable and preferred are triethanolamine, methyldiethanolamine, dimethylaminodiglycol, dimethylethanolamine, ethanolamine and/or N,N,N',N'-tetra (hydroxyethyl)ethylenediamine.

The resulting alkanolamine-containing foams are tacky. The tackiness can be completely eliminated by dusting with fine-particle powders. In principle, all organic or inorganic materials in the form of fine powders are suitable as long as they are hydrophilic, such as fine-particle silica (Aerosil®), silicates, talc, guar gum, tara flour, locust bean gum, all types of starches, crosslinked or uncrosslinked polyacrylic acids or salts thereof, polyvinyl alcohols, copolymers of maleic acid, titanium dioxide, zeolites, cellulose, carboxymethylcellulose and hydroxyethylcellulose. Water-insoluble materials are preferred, especially talc and Aerosil®. The dusting is expediently carried out after the polymerization. The application rates are, for example, between 0.01 and 10%, preferably between 0.1 and 5%, based on the weight of the foam.

The superabsorbent foams according to the invention have a density of, for example, 10–3 to 0.9, preferably 0.05 to 0.5, g/cm$^3$.

Determination of the Monomer Foam Density

Exactly 100 ml of the monomer foam are introduced into a measuring cylinder, and the weight of this volume of foam is determined. The density is obtained in g/cm$^3$ by dividing the weight in g by 100.

Determination of the Polymer Foam Density

The density of the superabsorbent foams is determined by gravimetry. Squares with sides 5 cm long are cut, for example with a sharp knife, out of a uniform foam layer with a defined thickness of between 3 and 5 mm. These samples are weighed, and the resulting weight is divided by the volume calculated from the dimensions.

Determination of the Absorption Capacity

The absorption capacity of the expanded superabsorbent for water per gram of superabsorbent is determined on pieces of foam having a thickness of 3 mm and each weighing 1 g. The absorption capacity is in this case tested by the teabag test. The liquid used is a 0.9% strength sodium chloride solution. 1 g of the expanded material is packed into a teabag which is then closed. Care must be taken that the teabag provides sufficient space for complete swelling. The teabag is then immersed in the liquid for a defined time, e.g. 30 min, and, after a drip time of, for example, 10 minutes, reweighed. To determine the blank value, a teabag without expanded superabsorbent is immersed in the solution, and the weight of the teabag is determined under the conditions described above. The absorption capacity then results from the following equation (1):

$$\text{Absorption capacity} = \frac{W_{TS} - W_T}{W_S}, \quad (1)$$

where $W_{TS}$ Weight of the teabag with superabsorbent foam $W_T$ Weight of the teabag in the blank test $W_S$ weight of the superabsorbent foam introduced

Determination of the Absorption Speed

The free absorption speed (referred to as FAS hereinafter) is found by cutting out, using a sharp knife, rectangular samples weighing 1 g from foam layers with a uniform thickness of 3 mm. These samples are placed in a Petri dish and 20 g of 0.9% strength sodium chloride solution are poured over. A stop clock is used to determine the time required by the foam sample to absorb the 0.9% strength sodium chloride solution completely. The absorption speed (FAS) in g/g·sec is calculated from the following equation (2):

$$FAS = 20 \text{ g}/[1 \text{ g·measured time in sec}] \quad (2)$$

Drop Absorption Speed (Referred to as DAS Hereinafter)

To determine the DAS, one drop of 0.9% strength sodium chloride solution is placed on the surface of the foam layer, and the time taken for the drop to be completely absorbed in the foam layer is measured. The same procedure is repeated for the second side of the foam layer, and the two values are indicated by top and bottom.

Vertical Wicking time (Referred to as VWT Hereinafter)

0.9% strength sodium chloride solution is introduced to a height of 0.5 cm into a Petri dish (diameter 10 cm, height 1 cm). A glass tube (diameter 1 cm, length 15 cm) is then sited a short distance above the base of the dish. A strip of foam with a length of 6 cm and a square base area (5×5 mm) is provided with a mark at 2.4 and 6 cm and placed inside the glass tube in the liquid. The time measurement is started at the same time. The time in seconds taken to reach the respective mark is determined.

The water-absorbing, expanded, crosslinked polymers described above can be used for all purposes for which expanded superabsorbents described in the literature are employed. They are used, for example, in hygiene articles employed to absorb body fluids and in dressing material for covering wounds. They are suitable, for example, as water-absorbing constituent in diapers, sanitary towels and incontinence articles. They can be employed in the form of composite materials. Expanded superabsorbents can additionally be used as sealing material, as soil improver, as soil substitute and as packaging material. Specific embodiments of articles which contain expanded superabsorbents are described in detail, for example, in WO-A-94/22502.

The foams described above can, by reason of their properties, carry out various functions in hygiene articles in the storage of body fluids:
acquisition
distribution and/or
storage The individual functions can be either assumed completely or assisted by other constituents, it thus being possible, for example, for the storage to be increased by adding superabsorbent granules, or the acquisition and distribution to be optimized by further constituents such as high loft nonwovens, polypropylene nonwovens, polyester nonwovens or chemically modified celluloses.

The percentage data in the examples are percent by weight unless otherwise evident from the context.

EXAMPLE 1

The following components were mixed in a beaker using a magnetic stirrer:

| | |
|---|---|
| 348.55 g | of acrylic acid (4.84 mol) |
| 135.51 g | of a 37.3% strength sodium acrylate solution in water (0.54 mol) |
| 28.00 g | of polyethylene glycol diacrylate of polyethylene glycol of molecular weight 400 |
| 21.33 g | of a 15% strength aqueous solution of an adduct of 80 mol of ethylene oxide and 1 mol of a linear saturated $C_{16}C_{18}$ fatty alcohol |
| 65.70 g | of water |

400.90 g (2.69 mol) of triethanolamine were added to the solution while cooling in ice in such a way that the internal temperature did not exceed 16° C. The resulting solution was transferred into a pressure vessel and saturated with carbon dioxide under a pressure of 12 bar for 25 min. Under pressure, 26.67 g of a 3% strength aqueous solution of 2,2'-azobis(2-amidinopropane) dihydrochloride were added and mixed in homogeneously using a powerful stream of carbon dioxide. Carbon dioxide was then passed through the reaction mixture for a further 5 min. The saturated reaction mixture was forced under a pressure of 12 bar through a nozzle with a diameter of 1 mm to form a fine-cell, free-flowing foam.

The resulting monomer foam was placed on a DIN A3-sized glass plate with edges 3 mm high and covered with a second glass plate. The foam sample was irradiated synchronously from both sides with two UV/VIS lamps (Höhnle UV 1000) for 4 minutes.

The resulting foam layer was completely dried in a vacuum oven at 70° C. To determine the properties, part of the foam was then adjusted to a moisture content of 10% by spraying with water.

| | |
|---|---|
| Solids content of the reaction mixture | 81.04% |
| Degree of neutralization | 60 mol % |
| Monomer foam density | 0.18 g/cm$^3$ |
| Polymer foam density | 0.19 g/cm$^3$ |
| Foam structure | homogeneous, completely open-celled, no skinning |

EXAMPLE 2

The following components were mixed in a beaker using a magnetic stirrer:

| | |
|---|---|
| 303.24 g | of acrylic acid (4.21 mol) |
| 117.90 g | of a 37.3% strength sodium acrylate solution in water (0.47 mol) |
| 24.36 g | of polyethylene glycol diacrylate of polyethylene glycol of molecular weight 500 |
| 5.57 g | of an adduct of 80 mol of ethylene oxide and 1 mol of a linear saturated $C_{16}C_{18}$ fatty alcohol |
| 0.15 g | of water |

348.79 g (2.69 mol) of triethanolamine were added to the solution while cooling in ice in such a way that the internal temperature did not exceed 16° C. The resulting solution was transferred into a pressure vessel and saturated with carbon dioxide under a pressure of 12 bar for 25 min. Under pressure, 13.92 g of a 3% strength aqueous solution of 2,2'-azobis(2-amidinopropane) dihydrochloride were added and mixed in homogeneously using a powerful stream of carbon dioxide. Carbon dioxide was then passed through the reaction mixture for a further 5 min. The saturated reaction mixture was forced under a pressure of 12 bar through a nozzle with a diameter of 1 mm to form a fine-cell, free-flowing foam.

The resulting monomer foam was dusted on both sides with about 0.3 g of talc and placed on a DIN A3-sized glass plate with edges 3 mm high and covered with a second glass plate. The foam sample was irradiated synchronously from both sides with two UV/VIS lamps (Höhnle UV 1000) for 4 minutes.

The resulting foam layer was dusted on both sides with about 0.3 g of talc and completely dried in a vacuum oven at 70° C. To determine the properties, part of the foam was then adjusted to a moisture content of 10% by spraying with water.

| | |
|---|---|
| Solids content of the reaction mixture | 88.67% |
| Degree of neutralization | 60 mol % |
| Monomer foam density | 0.19 g/cm$^3$ |
| Polymer foam density | 0.17 g/cm$^3$ |
| Foam structure | homogeneous, completely open-celled, no skinning |

EXAMPLE 3

The following components were mixed in a beaker using a magnetic stirrer:

| | |
|---|---|
| 278.84 g | of acrylic acid (3.87 mol) |
| 108.41 g | of a 37.3% strength sodium acrylate solution in water (0.43 mol) |
| 22.40 g | of polyethylene glycol diacrylate of polyethylene glycol of molecular weight 500 |
| 17.07 g | of a 15% strength aqueous solution of an adduct of 80 mol of ethylene oxide and 1 mol of a linear saturated $C_{16}C_{18}$ fatty alcohol |
| 5.12 g | of a 25% strength aqueous solution of the salt of diethanolamine and heptadecafluorooctanesulfonic acid |
| 52.56 g | of water |

320.72 g (2.15 mol) of triethanolamine were added to the solution while cooling in ice in such a way that the internal temperature did not exceed 16° C. The resulting homogeneous mixture was transferred into a pressure vessel and saturated with carbon dioxide under a pressure of 10 bar for 25 min. Under pressure, 21.33 g of a 3% strength aqueous solution of 2,2'-azobis(2-amidinopropane) dihydrochloride were added and mixed in homogeneously using a powerful stream of carbon dioxide. Carbon dioxide was then passed through the reaction mixture for a further 5 min. The saturated reaction mixture was forced under a pressure of 12 bar through a nozzle with a diameter of 1 mm to form a fine-cell, free-flowing foam.

The resulting monomer foam was placed on a DIN A3-sized glass plate with edges 3 mm high and covered with a second glass plate. The foam sample was irradiated synchronously from both sides with two UV/VIS lamps (Höhnle UV 1000) for 4 minutes.

The resulting foam layer was dusted on both sides with about 0.3 g of talc and completely dried in a vacuum oven at 70° C. To determine the properties, part of the foam was then adjusted to a moisture content of 10% by spraying with water.

| | |
|---|---|
| Solids content of the reaction mixture | 81.0% |
| Degree of neutralization | 60 mol % |
| Monomer foam density | 0.18 g/cm³ |
| Polymer foam density | 0.18 g/cm³ |
| Foam structure | homogeneous, completely open-celled, no skinning |

Comparative Example 1

The following components were mixed in a closed tube with screw closure using a magnetic stirrer:

| | |
|---|---|
| 37.64 g | of acrylic acid (0.52 mol) |
| 395.08 g | of a 37.3% strength sodium acrylate solution in water (1.57 mol) |
| 9.25 g | of guar gum |
| 1.85 g | of polyethylene glycol diacrylate of a polyethylene glycol of molecular weight 400 |
| 58.58 g | of a 15% strength aqueous solution of an adduct of 80 mol of ethylene oxide and 1 mol of a linear saturated $C_{16}C_{18}$ fatty alcohol |
| 6.85 g | of water |

The resulting homogeneous mixture was introduced into a closed 2 l flask with cooling jacket, into which carbon dioxide was passed from below. Two BOKU egg whisks connected via gears to an IKA RW28 W stirrer were inserted into the flask. The carbon dioxide stream was adjusted so that it bubbled at a rate of 100 l/h through the reaction mixture. The stirring motor was initially adjusted to a speed of 200 rpm, and carbon dioxide was passed through the mixture for 20 min to remove dissolved oxygen. During this time, the internal temperature was adjusted to 16° C with the aid of the cooling jacket and a thermostat. Then 4.63 g of pentane and 20.97 g of a 3% strength solution of 2,2'-azobis (2-amidinopropane) dihydrochloride in water were added and the stirrer speed was adjusted to 735 rpm. The mixture was beaten at this speed for 3.5 min. After the end of the beating period, a fine-cell, free-flowing foam was obtained.

The monomer foam was placed on a DIN A3-sized glass plate with edges 3 mm high and covered with a second glass plate. The foam sample was irradiated synchronously from both sides with two UV/VIS lamps (Höhnle UV 1000) for 4 minutes.

The resulting foam layer was completely dried in a vacuum oven at 70° C. and then adjusted to a moisture content of 25% by spraying with water.

| | |
|---|---|
| Solids content of the reaction mixture | 38.4% |
| Degree of neutralization | 75 mol % |
| Monomer foam density | 0.31 g/cm³ |
| Polymer foam density | 0.32 g/cm³ |
| Foam structure | homogeneous, completely open-celled, no skinning |
| Handle | moist, scarcely tacky |

Comparative Example 2

The following components were mixed in a closed tube with screw closure using a magnetic stirrer:

| | |
|---|---|
| 127.93 g | of acrylic acid (1.67 mol) |
| 93.43 g | of a 37.3% strength sodium acrylate solution in water (0.42 mol) |
| 12.60 g | of guar gum |
| 6.29 g | of polyethylene glycol diacrylate of a polyethylene glycol of molecular weight 400 |
| 58.78 g | of a 15% strength aqueous solution of an adduct of 80 mol of ethylene oxide and 1 mol of a linear saturated $C_{16}C_{18}$ fatty alcohol |
| 63.02 g | of water |

The resulting homogeneous mixture was introduced into a closed 2 l flask with cooling jacket and dropping funnel, into which carbon dioxide was passed from below. Two BOKU egg whisks connected via gears to an IKA RW28W stirrer were inserted into the flask. The carbon dioxide stream was adjusted so that it bubbled at a rate of 100 l/h through the reaction mixture. The stirring motor was initially adjusted to a speed of 200 rpm, and carbon dioxide was passed through the mixture for 20 min to remove dissolved oxygen. During this time, 152.42 g of triethanolamine (1.04 mol) was added dropwise with cooling so that a final temperature of 16° C. was reached.

Then 4.63 g of pentane and 20.99 g of a 3% strength solution of 2,2'-azobis(2-amidinopropane) dihydrochloride in water were added and the stirrer speed was increased to 735 rpm. The mixture was beaten at this speed for 3.5 min. After the end of the beating period, a fine-cell, free-flowing foam was obtained.

The resulting monomer foam was placed on a DIN A3-sized glass plate with edges 3 mm high and covered with a second glass plate. The foam sample was irradiated synchronously from both sides with two UV/VIS lamps (Höhnle UV 1000) for 4 minutes.

The resulting foam layer was dusted on both sides with about 0.3 g of talc and completely dried in a vacuum oven at 70° C. To determine the properties, part of the foam was then adjusted to a moisture content of 10% by spraying with water.

| | |
|---|---|
| Solids content of the reaction mixture | 63.6% |
| Degree of neutralization | 70 mol % |
| Monomer foam density | 0.26 g/cm$^3$ |
| Polymer foam density | 0.26 g/cm$^3$ |
| Foam structure | homogeneous, completely open-celled, no skinning |

Comparative Example 3 (Corresponding to Example 1 of JP-A-08073507)

A mixture was prepared from the following components in a closed flask with stirrer and nitrogen introduction from below:

| | |
|---|---|
| 180.00 g | of acrylic acid (2.50 mol) |
| 186.50 g | of triethanolamine (1.25 mol) |
| 86.18 g | of water |
| 4.60 g | of hydroxyethylcellulose |
| 4.00 g | of trimethylolpropane triacrylate |
| 3.33 g | of a 15% strength aqueous sodium peroxodisulfate solution |
| 2.50 g | of a 0.5% strength solution of ascorbic acid in water |

The resulting mixture was introduced between two Teflon plates held 1 mm apart by a rubber seal, and was completely polymerized in a circulating air oven at 80° C.

The resulting gel layer with a thickness of 0.9 mm had a solids content of 90% and was very tacky.

Comparative Example 4 (Corresponding to Example 9 of WO-A-95/02002)

| | |
|---|---|
| 641.56 g | of a 40.0% strength potassium acrylate solution in water (2.33 mol) |
| 235.00 g | of water |
| 72.06 g | of acrylic acid (1.00 mol) |
| 0.99 g | of triallylamine |

-continued

| | |
|---|---|
| 3.29 g | of polyvinyl alcohol |
| 0.82 g | of 2,2'-azobis(2-amidinopropane) dihydrochloride |

A reaction mixture was prepared from the above components in a beaker and was saturated with $CO_2$ by adding dry ice. The final temperature reached was 4° C. A layer 1 cm thick of the mixture was introduced into a cooled porcelain dish and was irradiated from above with a UV lamp (Höhnle UV 1000) for the polymerization.

The resulting foam layer was completely dried in a vacuum oven at 85° C. and then adjusted to a moisture content of 25% by spraying with water.

| | |
|---|---|
| Solids content of the reaction mixture | 35.00% |
| Degree of neutralization | 70.00 mol % |
| Monomer foam density | cannot be determined |
| Polymer foam density | 0.60 g/cm$^3$ |
| Foam structure | homogeneous, completely closed-cell, extensive skinning on both sides |

Comparative Example 5 (Corresponding to Example 9 of WO-A-95/02002)

The foam of Comparative example 4 was comminuted, dried in a vacuum oven at 85° C. and ground, and the fraction with a particle size between 90 and 850 μm was removed.

This powder was sprayed with a mixture of 0,5% 1,3-dioxolan-2-one, 2.0% water and 2.0% ethanol, in each case based on the powder, and heated at 200° C. for 30 min. The properties of this SAP are indicated in the tables.

Comparative Example 6 (Corresponding to Example 2 of U.S. Pat. No. 5,750,585)

| | |
|---|---|
| 6.00 g | of water |
| 1.98 g | of acrylic acid (1.00 mol) |
| 0.02 g | of N,N'-methylenebisacrylamide |
| 0.50 g | of a 10% strength aqueous solution of N,N,N',N'-tetramethylethylenediamine |

A solution was prepared from the indicated constituents and was introduced into a test tube with a diameter of 30 mm, and then 0.5 ml of a 10% strength aqueous solution of ammonium persulfate was added and mixed in by shaking. The solution was heated to 60° C. by immersion in a water bath and then removed from the water bath. Then 1 ml of a 70% strength suspension of $NaHCO_3$ in water was added dropwise, during which the test tube was shaken. The resulting foam was removed from the test tube, completely dried and then adjusted to a moisture content of 25% by spraying with water.

Further use properties of the polymers described in the above examples and comparative examples are compiled in the following tables. They show that the products according to the invention have significantly better absorption characteristics and distributing action.

TABLE 1

Absorption capacities

| Example | Absorption capacity [g/g] | Moisture content [%] | Absorption capacity for 100% solids content [g/g] |
|---|---|---|---|
| 1 | 58.3 | 10 | 64.8 |
| 2 | 57.9 | 10 | 64.3 |
| 3 | 53.8 | 25 | 71.1 |
| Comparative example 1 | 36.2 | 25 | 48.3 |
| Comparative example 2 | 55.9 | 10 | 62.1 |
| Comparative example 3 | 14.3[a]/24, 3[b] | 10 | 18.8[a]/27.0[b] |
| Comparative example 4 | 7.5 | 25 | 10.0 |
| Comparative example 5 | 45, 3 | <1 | 60.4 |
| Comparative example 6 | 25, 6 | 25 | 34.1 |

[a] The absorptions were determined after a swelling time of 60 min
[b] The absorptions were determined after a swelling time of 18 h

TABLE 2

Absorption characteristics based on absorption speeds

| Example | FAS [g/g sec] | DAS top/bottom [sec] |
|---|---|---|
| 1 | 10.00 | <1/<1 |
| 2 | 6.67 | <1/<1 |
| 3 | 4.00 | <1/<1 |
| Comparative example 1 | 0.79 | 9/11 |
| Comparative example 2 | 3.25 | 2/2 |
| Comparative example 3 | <0.02 | >100/>100 |
| Comparative example 4 | <0.02 | >100/>100 |
| Comparative example 5 | 0.52 | a) |
| Comparative example 6 | <0.05 | 14/35 | a) cannot be determined on a powder

TABLE 3

Distributing action based on wicking characteristics

| | Vertical wicking | | |
|---|---|---|---|
| Example | 2 cm [sec] | 4 cm [sec] | 6 cm [sec] |
| 1 | 8 | 23 | 48 |
| 2 | 7 | 24 | 46 |
| 3 | 10 | 32 | 68 |
| Comparative example 1 | 128 | 600 | >600 |
| Comparative example 2 | 12 | 77 | 162 |
| Comparative example 3 | >600 | >600 | >600 |
| Comparative example 4 | 215 | >600 | >600 |
| Comparative example 5 | a) | a) | a) |
| Comparative example 6 | 228 | >600 | >600 | a) cannot be determined on a powder

We claim:

1. An expanded, crosslinked polymer which has a free absorption speed (FAS) for a 0.9% aqueous sodium chloride solution of from 4.0 to 100 g/g sec, obtained by
   (I) foaming a polymerizable aqueous mixture which comprises
      (a) one or more monoethylenically unsaturated monomers which contain acidic groups or monoethylenically unsaturated monomers which contain acidic groups neutralized with alkali metal bases, ammonia or amines,
      (c) one or more crosslinkers,
      (d) one or more initiators and
      (e) 0.1–20% by weight of at least one surfactant,
         where the foaming takes place by dissolving a gas which is inert to free radicals under a pressure of 2–400 bar in the polymerizable aqueous mixture, and then decompressing the aqueous mixture to atmospheric pressure, and
   (II) polymerizing the foamed mixture to form an expanded hydrogel.

2. The polymer as claimed in claim 1, obtained by
   (I) foaming a polymerizable aqueous mixture which comprises
      (a) one or more monoethylenically unsaturated monomers which contain acidic groups from 15 to 90 mol % neutralized with alkali metal bases, ammonia or amines,
      (b) one or more other monoethylenically unsaturated monomers,
      (c) one or more crosslinkers,
      (d) one or more initiators,
      (e) 0.1–20% by weight of at least one surfactant,
      (f) at least one solubilizer and
      (g) one or more thickeners, foam stabilizers, polymerization regulators, fillers and/or cell nucleating agents,
         where the foaming takes place by dissolving a gas which is inert to free radicals under a pressure of 2–400 bar in the polymerizable aqueous mixture, and then decompressing the aqueous mixture to atmospheric pressure, and
   (II) polymerizing the foamed mixture to form an expanded hydrogel and adjusting the water content of the expanded polymer to 1–60% by weight.

3. The polymer as claimed in claim 1, which is obtained by neutralizing the monomers (a) which contain acidic groups with tertiary alkanolamines and/or by neutralizing the free acidic groups of the expanded hydrogel after the polymerization with at least one alkanolamine, wherein the degree of neutralization is at least 20 mol % in each case.

4. The polymer as claimed in claim 1, wherein the degree of neutralization is at least 40 mol %.

5. The polymer as claimed in claim 1, which has a vertical wicking time (VWT=time for a 0.9% by weight aqueous sodium chloride solution to spread vertically in a foam) of 0.2–120 seconds for a height of 4 cm.

6. A process for producing expanded, crosslinked polymers, comprising
    foaming a polymerizable mixture of
        (a) one or more monoethylenically unsaturated monomers which contain acidic groups or monoethylenically unsaturated monomers which contain acidic groups neutralized with alkali metal bases, ammonia or amines,
        (c) one or more crosslinkers,
        (d) one or more initiators and
        (e) 0.1–20% by weight of at least one surfactant,
            to form a foam in a first stage with a gas which is inert to free radicals, and in a second stage polymerizing the foam to form an expanded hydrogel, where in the first stage a gas which is inert to free radicals is dissolved under a pressure of 2–400 bar in the polymerizable aqueous mixture, and the aqueous mixture is then decompressed to atmospheric pressure to form a foam.

7. The process as claimed in claim 6, wherein the polymerizable aqueous mixture is saturated with carbon dioxide or nitrogen under a pressure of 5–40 bar.

8. The process as claimed in claim 6, wherein at least 20 mol % of the monomers (a) which contain acidic groups are neutralized with tertiary alkanolamines and/or the free acidic groups of the expanded hydrogel are at least 20 mol % neutralized with at least one alkanolamine after the polymerization.

9. The process as claimed in claim 6, wherein at least 40 mol % of the monomers (a) which contain acidic groups are neutralized with tertiary alkanolamines and/or the free acidic groups of the expanded hydrogel are at least 40 mold neutralized with at least one alkanolamine after the polymerization.

10. The process as claimed in claim 6, wherein triethanolamine, ethanolamine and/or N,N,N',N'-tetra(hydroxyethyl)ethylenediamine are employed as alkanolamines.

11. A method comprising
    absorbing body fluids with one or more of a dressing material for covering wounds, a sealing material, a soil improver, a soil substitute or a packaging material comprising the polymer as claimed in claim 1.

12. A hygiene article employed to absorb body fluids, in dressing material for covering wounds, as sealing material, as soil improver, as soil substitute and as packaging material comprising the water-absorbing, expanded, crosslinked polymers as claimed in claim 1.

13. The polymer as claimed in claim 1, wherein at least 1.0 g of the inert gas is dissolved per kilogram of the polymerizable mixture.

14. The process as claimed in claim 6, wherein at least 1.0 g of the inert gas is dissolved per kilogram of the polymerizable mixture.

15. The polymer as claimed in claim 1, wherein the inert gas is selected from the group consisting of carbon dioxide, nitrogen, dinitrogen monoxide and mixtures thereof.

16. The process as claimed in claim 6, wherein the inert gas is selected from the group consisting of carbon dioxide, nitrogen, dinitrogen monoxide and mixtures thereof.

17. The polymer as claimed in claim 1, wherein the decompressing is carried out in one or more pressure drops.

18. The process as claimed in claim 6, wherein the decompressing is carried out in one or more pressure drops.

* * * * *